US007423009B2

(12) United States Patent
Nakagawa et al.

(10) Patent No.: US 7,423,009 B2
(45) Date of Patent: Sep. 9, 2008

(54) METHOD FOR TREATMENT OF KIDNEY DISEASES

(75) Inventors: Takashi Nakagawa, Tokyo (JP); Hiroyuki Ishiwata, Chiba (JP); Toshiaki Takizawa, Tokyo (JP); Toru Kanke, Tokyo (JP); Yasushi Wada, Tokyo (JP); Junichi Kawagoe, Saitama (JP)

(73) Assignee: Kowa Company, Ltd., Nagoya-shi (JP)

( * ) Notice: Subject to any disclaimer, the term of this patent is extended or adjusted under 35 U.S.C. 154(b) by 489 days.

(21) Appl. No.: 10/673,380

(22) Filed: Sep. 30, 2003

(65) Prior Publication Data

US 2004/0132635 A1    Jul. 8, 2004

Related U.S. Application Data

(60) Provisional application No. 60/414,412, filed on Sep. 30, 2002.

(51) Int. Cl.
*A61K 38/00* (2006.01)
*A61K 38/43* (2006.01)
*A61K 38/48* (2006.01)

(52) U.S. Cl. .......................... 514/2; 424/94.1; 424/94.64
(58) Field of Classification Search ........................ None
See application file for complete search history.

(56) References Cited

FOREIGN PATENT DOCUMENTS

WO    WO 01/74390 A2    10/2001

OTHER PUBLICATIONS

Rondeau, et al, 2001, Nephrol. Dial. Transplant., 16: 1529-1531.*
Gee, et al, 1985, Biochem., 228: 119-126.*
Bertog, Marko, et al. "Basolateral proteinase-activated receptor (PAR-2) induces chloride secretion in M-1 mouse renal cortical collecting duct cells". *Journal of Physiology* (1999), 521-1, pp. 3-17.
Gui, Yu, et al. "Bidirectional regulation of renal hemodynamics by activation of PAR₁ and PAR₂ in isolated perfused rat kidney." *Am J Physical Renal Physiol* 285: F95-104, 2003.
Trottier, Greg, et al. "PAR-2 elicits afferent arteriolar vasodilation by NO-dependent and NO-independent actions." *Am J Physical Renal Physiol* 282: F891-897, 2002.
Grandaliano, Giuseppe, et al. "Protease-Activated Receptor 2 Expression in IgA Nephropathy: A Potential Role in the Pathogenesis of Interstitial Fibrosis." *J Am Soc Nephrol* 14: 2072-2083, 2003.
LeHir, Michel, et al. "IL-12-Dependent, IFN-γ-Independent Experimental Glomerulonephritis." *Kidney Blood Press Res* 2001; 24-27-32.
Ito, Mikio, et al. "Crescentic Type Nephritis Induced By Anti-Glomerular Basement Membrane (GBM) Serum in Rats." *Japan J. Pharmacol.* 33, 1145-1154 (1983).
Kawabata, Atsufumi, et al. "Activation of Protease-Activated Receptor-22 (PAR-2) Triggers Mucin Secretion in the Rat Sublingual Gland." *Biochemical and Biophysical Research Communications* 270, 298-302 (2000).

Bahjat, Al-Ani, et al. "Detection of functional receptors for the proteinase-activated-receptor-2-activating polypeptide, SLIGRL-NH₂, in rat vascular and gastric smooth muscle." *Can. J. Physiol. Pharmacol.* vol. 73, 1203-1207 (1995).
Kong, Wuyi, et al. "Luminal trypsin may regulate enterocytes through proteinase-activated receptor 2." *Proc. Natl. Acad. Sci., USA* vol. 94 pp. 8884-8889 (Aug. 1997).
Molino, Maria, et al. "Endothelial Cell Thrombin Receptors and PAR-2." *The Journal of Biological Chemistry* vol. 272, No. 17 pp. 11133-11141 (Apr. 25, 1997).
Ferrell, William R., et al. "Essential role for proteinase-activated receptor 2 in arthritis." *The Journal of Clinical Investigation* vol. 111, No. 1 (Jan. 2003).
Kawagoe, Junichi, et al. "Effect of Protease-Activated Receptor-2 Deficiency on Allergic Dermatitis in the Mouse Ear." *Japan J. Pharmacol.* 88, 77-84 (2002).
Lindner, Jonathan, et al. "Delayed Onset of Inflammation in Protease-Activated-Receptor-2-Deficient Mice." *The Journal of Immunology* pp. 6504-6510, Copyright 2000 by the American Association of Immunologists.
Kanke, Toru, et al. "Proteinase-activated Receptor-2 mediated Activation of Stress-activated Protein Kinases and Inhibitory κB Kinases in NCTC 2544 Keratinocytes." *The Journal of Biological Chemistry*, vol. 276, No. 34, pp. 31657-31666 (Aug. 24, 2001).
Hou, L., et al. "Immunolocalization of protease-activated receptor-2 in skin: receptor activation stimulates interleukin-8 secretion by keratinocytes in vitro." *Immunology* 94, 356-362, Copyright 1998 Blackwell Science Ltd.
Compton, Steven J. et al. "The Role of Mast Cell Tryptase in Regulating Endothelial Cell Proliferation, Cytokine Release, and Adhesion Molecule Expression: Tryptase Induces Expression of mRNA for IL-1β and IL-8 and Stimulates the Selective Release of IL-8 from Human Umbilical Vein Endothelial Cells." *The Journal of Immunology*, pp. 1939-1946, Copyright 1998 by the American Association of Immunologists.
He, Shaoheng, et al. "Potent Induction of a Neutrophil and Eosinophil-Rich Infiltrate In Vivo by Human Mast Cell Tryptase: Selective Enhancement of Eosinophil Recruitment by Histamine." *The Journal of Immunology*, pp. 6216-6225, Copyright 1997 by the American Association of Immunologists.

(Continued)

*Primary Examiner*—Elizabeth C. Kemmerer
*Assistant Examiner*—Sandra Wegert
(74) *Attorney, Agent, or Firm*—Westerman, Hattori, Daniels & Adrian, LLP.

(57) ABSTRACT

The present invention relates to a composition for prevention and treatment of kidney diseases comprising one or more effective component(s) of a PAR-2 activating agent which is able to activate PAR-2 and a pharmaceutically acceptable carrier. The present invention further relates to a method for prevention and treatment of kidney diseases comprising administration of a composition for prevention and treatment of kidney diseases containing a PAR-2 activating agent which is able to activate PAR-2 to patients suffering from kidney diseases, and also relates to the use of a PAR-2 activating agent which is able to activate PAR-2 for the manufacture of a composition for prevention and treatment of kidney diseases. The present invention furthermore relates to a method for screening an effective ingredient for prevention and treatment of kidney diseases comprising screening of the activating action of the test substance to PAR-2.

2 Claims, 7 Drawing Sheets

OTHER PUBLICATIONS

Vergnolle, Nathalie "Proteinase-Activated Receptor-2-Activating Peptides Induce Leukocyte Rolling, Adhesion, and Extravasation in Vivo." *The Journal of Immunology*, pp. 5064-5069, Copyright 1999 by the American Association of Immunologists.

Steinhoff, M., et al. "Agonists of proteinase-activated receptor 2 induce inflammation by a neurogenic mechanis,." *Nature Medicine* vol. 6, No. 2 (Feb. 2000).

He, Shaoheng and Walls, A. "Human mast cell tryptase: a stimulus of microvascular leakage and mast cell activation." *European Journal of Pharmacology*, 328 (1997) 89-97.

Vergnolle, Nathalie, et al. "Characterization of the inflammatory response to proteinase-activated receptor-2 ($PAR_2$)-activating peptides in the rat paw." *British Journal of Pharmacology* (1999) 127, 1083-1090.

Kawabata, Atsufumi, et al. "Increased vascular permeability by a specific agonist of protease-activated receptor-2 in rat hindpaw." *British Journal of Pharmacology* (1998) 125, 419-422.

Smith-Swintosky, et al. "Protease-Activated Receptor-2 (PAR-2) Is Present in the Rat Hippocampus and Is Associated with Neurodegeneration." *Journal of Neurochemistry* pp. 1890-1896 Copyright 1997 International Society for Neurochemistry.

Damiano, Bruce P., et al. "Increased Expression of Protease Activated Receptor-2 (PAR-2) in Balloon-Injured Rat Cartotid Artery." *Thromb Haemost* 1999; 81:808-14.

Cicala, Carla, et al. "Protease-Activated Receptor-2 Involvement in Hypotension in Normal and Endotoxemic Rats in Vivo." www.circulationaha.org. Circulation May 1999, vol. 99: 2590-2597.

MacFarlane, Scott R., et al. "Proteinase-Activated Receptors." *Pharmacol Rev* 53:245-282, 2001.

Roy, Samir. S., et al. "Dual endothelium-dependent vascular activities of proteinase-activated receptor-2-activating peptides: evidence for receptor heterogeneity." *British Journal of Pharmacology* (1998) 123, 1434-1440.

Matsui-Nakanishi, Mayumi, et al. "PAR3 is a cofactor for PAR4 activation by thrombin." *Nature* vol. 404, pp. 609-613 Apr. 6, 2000.

Nystedt, Sverker, et al. "Molecular cloning of a potential proteinase activated receptor." *Proc. Natl. Acad. Sci. USA* vol. 91, pp. 9208-9212, Sep. 1994.

Koichi Hayashi et al., *Antihypertensive Drugs (Kouatsuyaku)—Treatement of Hypertension Involving Renal Damage*, Igaku No Ayumi, kidney diseases (Jinshikkan)—state of arts (Ver. 2), Ishiyaku Publishers, Inc., 1997, pp. 158-161.

European Search Report dated Jul. 7, 2007 in PCT/JP0312472.

Sebekova et al.: "Systemic treatment with proteolytic enzymes in rat models of nonimmune mediated :renal diseases" International Journal of Immunotherapy, Bioscience Ediprint Inc., vol. 13, No. 3/4, 1997, pp. 79-83.

Emancipator et al.: "Oral enzymes in different animal models of glomerulonephritis", International Journal of Immunotherapy, Bioscience Ediprint Inc., vol. 13, No. 3/4, 1997, pp. 97-103.

Damioan Bruce P et al.: "Cardiovascular responses mediated by protease-activated receptor-2 (PAR-2) and thrombin receptor (PAR-1) are distinguished in mice deficient in PAR-2 or PAR-1", Journal of Pharmacology and Experimental Therapeutics, vol. 288, No. 2, Feb. 1999, pp. 671-678, Damiano, Bruce P.

Cocks T M et al.: "A protective role for protease-activated receptors in the airways", Nature, Nature Publishing Group, London, GB, vol. 398, Mar. 11, 1999, pp. 156-160.

Sobey Christopher G et al.: "Activation of 1-5 protease-activated receptor-2 (PAR-2) elicits nitric oxide-dependent dilatation of the basilar artery in vivo", Stroke, vol. 29, No. 7, Jul. 1998, pp. 1439-1444.

Kawabata Atsufumi et al.: "The protease-activated reception-2 agonist induces gastric mucus secretion and mucosal cytoprotection", Journal of Clinical Investigation, vol. 107, No. 11, Jun. 2001, pp. 1443-1450.

Imanishi et al.: "Glomereular hypertension as one cause of albuminuria in Type II diabetic patients", Diabetologia, Berlin, DE, vol. 42, No. 8, Aug. 1999, pp. 999-1005.

* cited by examiner

METHOD FOR TREATMENT OF KIDNEY DISEASES

This application claims benefit of U.S. provisional application number 60/414,412, filed Sep. 30, 2002 under 35 U.S.C. §119 (e).

TECHNICAL FIELD

The present invention relates to a method for prevention and treatment of kidney diseases by administration of a composition for prevention and treatment of kidney diseases containing a PAR-2 activator as an effective ingredient to patients suffering from kidney diseases. The present invention further relates to a method for screening of an effective ingredient for prevention and treatment of kidney diseases where a PAR-2 activating action of a test drug is screened.

BACKGROUND OF THE INVENTION

Kidney is a urinary organ of vertebrate animals and comprises a pair of left and right ones at the back of somatic cavity. Renal artery comes in from the concave at the inner side of its center called hilum of kidney and renal vein and ureter comes out therefrom. An inner part of parenchyma of the kidney consists of cortex and medulla. Medulla comprises ten and several complexes and the front end thereof forms nipple. In the cortex, glomerulus is present. The glomerulus is a spherical block of capillaries having a diameter of about 200 µm and carries out filtration of blood. A functional unit of the kidney is called nephron and about one million nephrons are present in one kidney. The nephron comprises glomerulus, capsule of Bowman covering that and proximal convoluted tubule, loop of Henle and distal tubule connecting thereto. The nephron joins a collecting tubule and the collecting tubule opens to renal pelvis at papillary tube via Belluni tube. Urine filtered by the glomerulus is subjected to re-absorption and secretion when passing through the urinary tubule whereupon the final urine is formed. As a result of formation of urine as such, the kidney maintains the homeostasis of internal environment of living body such as 1) excretion of water, 2) excretion of final products of metabolism, particularly nitrogen-containing components, 3) excretion of electrolytes, 4) excretion of heterogeneous substances to body, 5) adjustment of osmotic pressure of blood, volume of body fluid, equilibrium between acid and base, etc. Further, the kidney is an organ which participates in adjustment of blood pressure by way of production and secretion of renin and prostaglandin and also in production of erythrocytes in bone marrow by way of production of erythropoietin.

Generally, kidney diseases are roughly classified into glomerular disease where disorder is noted in glomerulus and tubular diseases where disorder is noted in urinary tubule. Although no effective drug is available at present for the treatment of kidney diseases, there have been clinically used steroids, immunosuppressants, anti-platelet agents/anticoagulants, prostaglandin preparations, hypotensive/diuretic preparations, etc. Among them, steroids are particularly commonly used, but on the other hand, severe side effects such as cataract and osteoporosis by the use of steroids have been known. In nephritis to which drugs are not applicable, treatment for the purpose of retarding the transfer to chronic renal failure has been done by, for example, means of dietary restriction (low-protein meals). Anyway, when nephritis becomes chronic and progressive, treatment is difficult and, finally, renal failure is resulted whereby dialysis of blood has to be forcibly applied. Dialysis of blood causes much burden to patients both economically and physically and, as the dialyzing period becomes long, may result in a problem such as expression of complication with other diseases (such as cerebral and cardiac diseases). In addition, from a social view, enormous medical cost for dialysis is needed and, therefore, there has been a brisk demand for the development of new and useful drugs which inhibit or retard the transfer to dialysis.

PAR (protease-activated receptor)—2 is a protease receptor which is a member of a family of G protein conjugation type receptor of a seven-transmembrane type.

With regard to PAR, four types—PAR-1, PAR-2, PAR-3 and PAR-4— have been cloned up to now and they belong to a receptor family mediating the action of serine proteases such as thrombin and trypsin on various kinds of cells. With regard to each of PAR-1, PAR-3 and PAR-4, its function has been clarified as a receptor relating to platelet coagulation by thrombin while, with regard to PAR-2, although it has many common points with other PARs in terms of structure and activation mechanism, it is different from other PARs in terms of function such as that it is not activated by thrombin and it is activated by trypsin or tryptase.

In those PARs, specific site of amino acid sequence of N-terminal of PAR molecule is cleaved by the action of thrombin or protease and the newly exposed cleaved terminal bonds to the bonding site of the receptor per se whereupon the receptor is activated. Outline of the amino acid sequence which activates the receptor at the cleaved site is shown by means of a one-letter expression of amino acid.

| PAR-1 | SFLLRN-NH$_2$ | (human) |
| PAR-2 | SLIGKV-NH$_2$ | (human) |
|       | SLIGRL-NH$_2$ | (mouse) |
| PAR-3 | (none)        |         |
| PAR-4 | GYPGQV        | (human) |
|       | GYPGKF        | (mouse) |

PAR-1, PAR-2 and PAR-4 are able to be non-enzymatically activated by exogenous peptide having an amino acid sequence of the cleaved site while PAR-3 is unable to be activated by such an exogenous peptide. In recent studies, it was proved that mouse PAR-3 per se is not activated but is a co-factor for PAR-4 which is able to function only in the co-presence with PAR-4 (Nature, 404, 609-613, 2000).

PAR-2 was cloned in 1994 by Nystedt, et al. (*Proc. Natl. Acad. Sci. USA*, 91, 9208-9212, 1994) and has been known to be activated by synthetic peptide having the same sequence as the above PAR-2 ligand, trans-cinnamoyl-LIGRLO-NH$_2$ which is a derivative thereof (*Br. J. Pharmacol.*, 123, 1434-1440, 1998), trypsin, tryptase, tissue factor/VIIa factor, Xa factor, acrosin which is a kind of sperm protease and trypsin-like serine protease identified from brain of rat (*Pharmacological Rev.*, 53, 245-282, 2001).

Physiological significance of activation of PAR-2 and its participation in pathology have been investigated in various kinds of cells, tissues and animal models and it has been reported that rolling and adhesion of leukocytes, infusion of neutrophils, secretion of inflammatory cytokines and leakage of plasma protein are induced and that onset and worsening of arteriosclerosis, dermatitis and acute inflammation are induced in experimental systems of in vitro and in vivo (*Circulation*, 99, 2590-2597, 1999; *Thromb. Haemost.*, 81, 808-814, 1999; *J. Neurochem.*, 69, 1890-1896, 1997; *Br. J. Pharmacol.*, 125, 419-422, 1998; *Br. J. Pharmacol.*, 127, 1083-1090, 1999; *Eur. J. Pharmacol.*, 328, 89-97, 1997; *Nat. Med.*, 6, 151-158, 2000; *J. Immunol.*, 163, 5064-5069, 1999; *J. Immunol.*, 159, 6216-6225, 1997; *J. Immunol.*, 161, 1939-1946, 1998; *Immunology*, 94, 356-362, 1998; *J. Biol. Chem.* 276, 31657-31666, 2001; *J. Immunol.*, 165, 6504-6510, 2000; *Jpn. J. Pharmacol.*, 88, 77-84, 2002). All these reports show that activation of PAR-2 induces inflammation and worsens it. As such, it has not been expected at all that activation of PAR-2 tends to suppress a certain type of inflammation. It has been also unknown at all that activation of PAR-2 is effective for prevention and treatment of kidney diseases.

DISCLOSURE OF THE INVENTION

The present inventors have investigated the effect of PAR-2 gene deficiency on experimental nephritis of mice and found that, as compared with mice of a wild type, progress of nephritis is significantly worsened in mice lacking in PAR-2 gene (PAR-$2^{-/-}$). It has been further found that, in the same model using wild type mice, nephritis is strongly more suppressed by a PAR-2 activator than by steroids which are widely used for the treatment of nephritis in clinic. From those results, it has been found that, in addition to a primary nephritis (mesangial proliferaqtive nephritis, etc.) where protopathic disorder is generated in kidney, PAR-2 activation which was known to have an inflammation-inducing action is effective for prevention and treatment of secondary nephritis (diabetic nephropathy, etc.) where disorder is generated in kidney caused by other diseases whereupon the present invention has been achieved. In addition, since activation of PAR-2 is effective for maintenance and recovery of renal functions, it has been found that an effect for retarding the transfer from renal failure to dialysis can be also expected.

Accordingly, the present invention provides a composition for prevention and treatment of kidney diseases by activation of PAR-2 and a method for prevention and treatment of kidney diseases using the same. The present invention further provides a method for screening the agent for prevention and treatment of kidney diseases where activation of PAR-2 is used as an index.

Thus, the present invention provides a composition for prevention and treatment of kidney diseases comprising one or more effective component(s) of a PAR-2 activating agent which is able to activate PAR-2 and a pharmaceutically acceptable carrier. The present invention further provides a method for prevention and treatment of kidney diseases comprising administration of a composition for prevention and treatment of kidney diseases containing a PAR-2 activating agent which is able to activate PAR-2 to patients suffering from kidney diseases. The present invention still further provides the use of a PAR-2 activating agent which is able to activate PAR-2 for the manufacture of a composition for prevention and treatment of kidney diseases.

The present invention furthermore provides a method for screening an effective ingredient for prevention and treatment of kidney diseases comprising screening of the activating action of the test substance to PAR-2.

BEST MODE FOR CARRYING OUT THE INVENTION

The present inventors have investigated the relation between nephritis induced by anti-GBM (GBM: glomerular basement membrane) antibody and PAR-2 using a male PAR-2 gene deficient mouse (homo-deficient mouse: PAR-$2^{-/-}$ mouse) which is a hybrid of self-proliferated 13-weeks-age C57BL/6 with 129/O1a.

Figure 1:
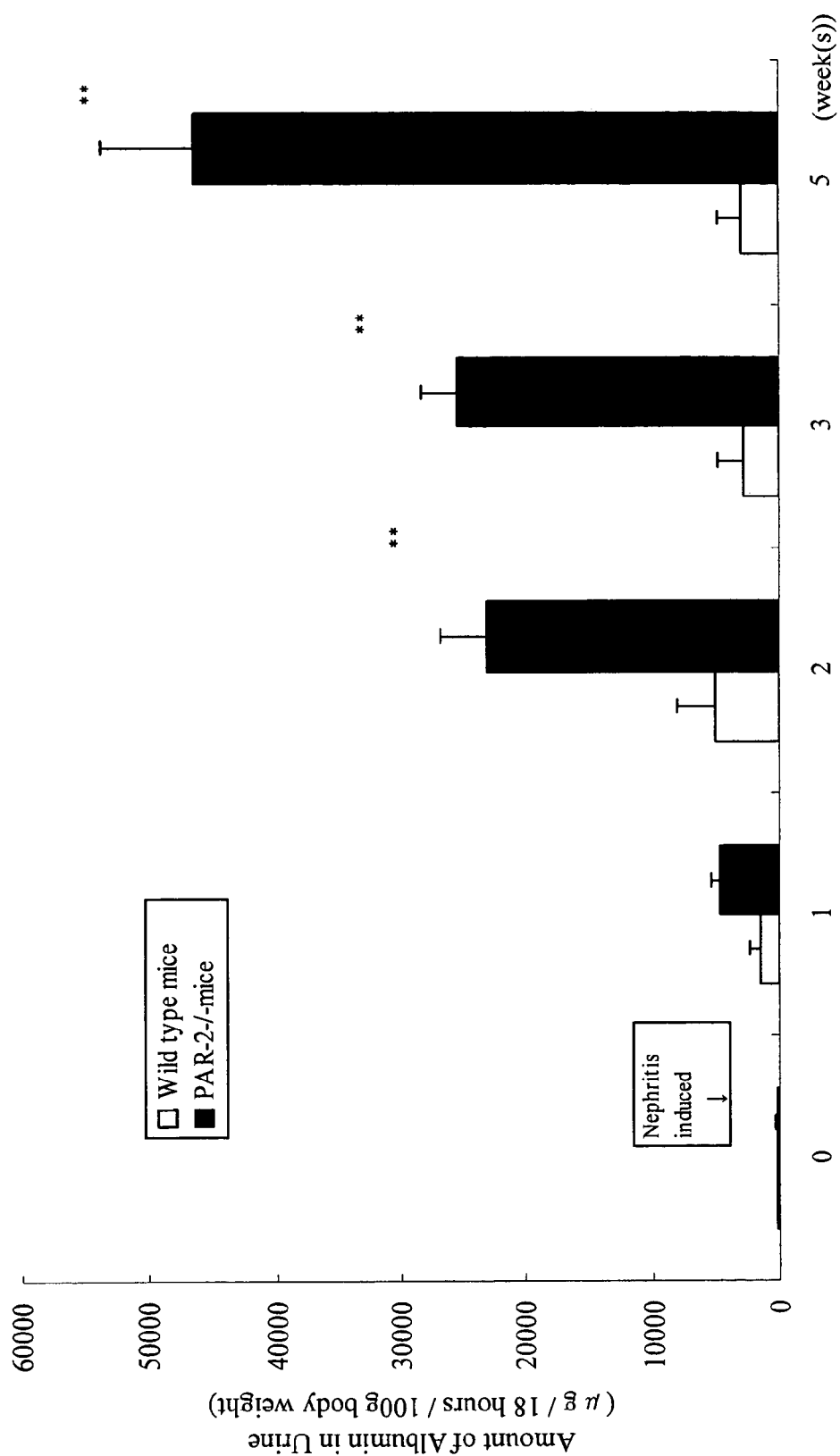
FIG. 1 shows changes with the passage of time of amount of albumin in urine in wild type mouse and PAR-$2^{-/-}$ mouse where nephritis was induced.

Changes with the passage of time of the amount of albumin in urine which is an index for nephritis is shown in FIG. 1. Ordinate of FIG. 1 shows the amount of albumin in urine (μg/18 hours/100 g body weight) while abscissa shows the period (weeks) from a single administration of rabbit antiserum (anti-GBM antiserum; 0.4 ml per mouse) to glomerular basement membrane (GBM) of mouse having titer of antibody of about 16-fold into tail vein. A white square in FIG. 1 shows the case of wild type mouse while a black square therein shows the case of PAR-$2^{-/-}$ mouse. Each value in FIG. 1 shows mean value ± standard error where * shows that there is a statistically significant difference of $p<0.05$ in comparison with the wild type mouse while ** shows that there is a statistically significant difference of $p<0.01$ in comparison with the wild type mouse.

It was found as a result that there was no statistically significant difference in albumin amounts in urine between untreated wild type mouse and PAR-$2^{-/-}$ mouse to which no anti-GBM antiserum was administered while that the amount of albumin in urine of PAR-$2^{-/-}$ mouse to which anti-GBM antiserum was administered significantly increased after one week from administration of the anti-GBM antiserum as compared with the case of wild type mouse and it increased significantly after two, three and even five weeks. Thus, it was noted that, as a result of deficiency of functions of PAR-2 due to deficiency of PAR-2 gene, kidney was significantly deteriorated in terms of its functions and, moreover, degree of nephritis was progressed with the passage of time.

Figure 2:
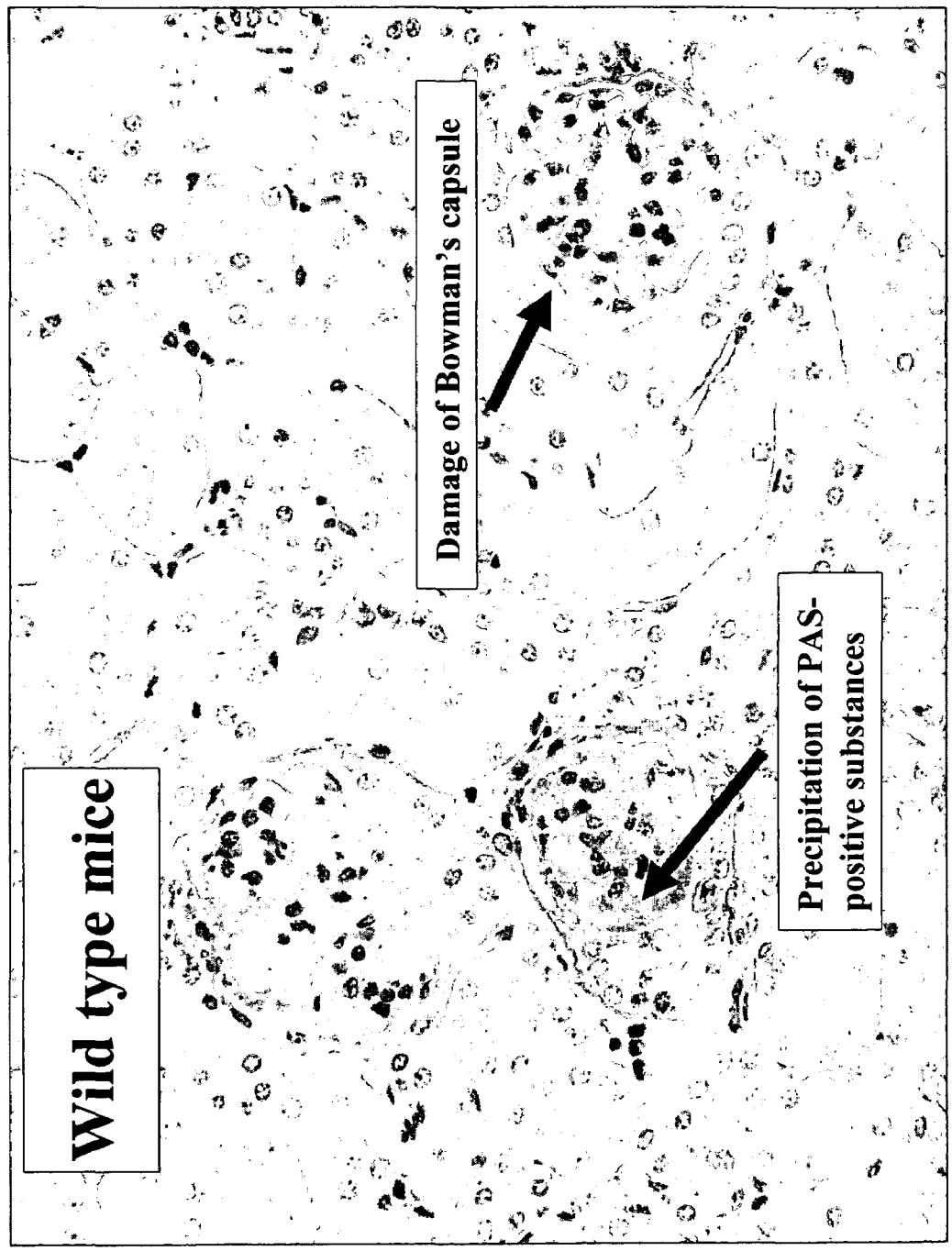
FIG. 2(a) is a histopathological image of kidney (glomeruli) in wild type mouse after five weeks from induction of nephritis.
FIG. 2(b) is a histopathological image of kidney (glomeruli) in PAR-$2^{-/-}$ mouse after five weeks from induction of nephritis.
Figure 2:
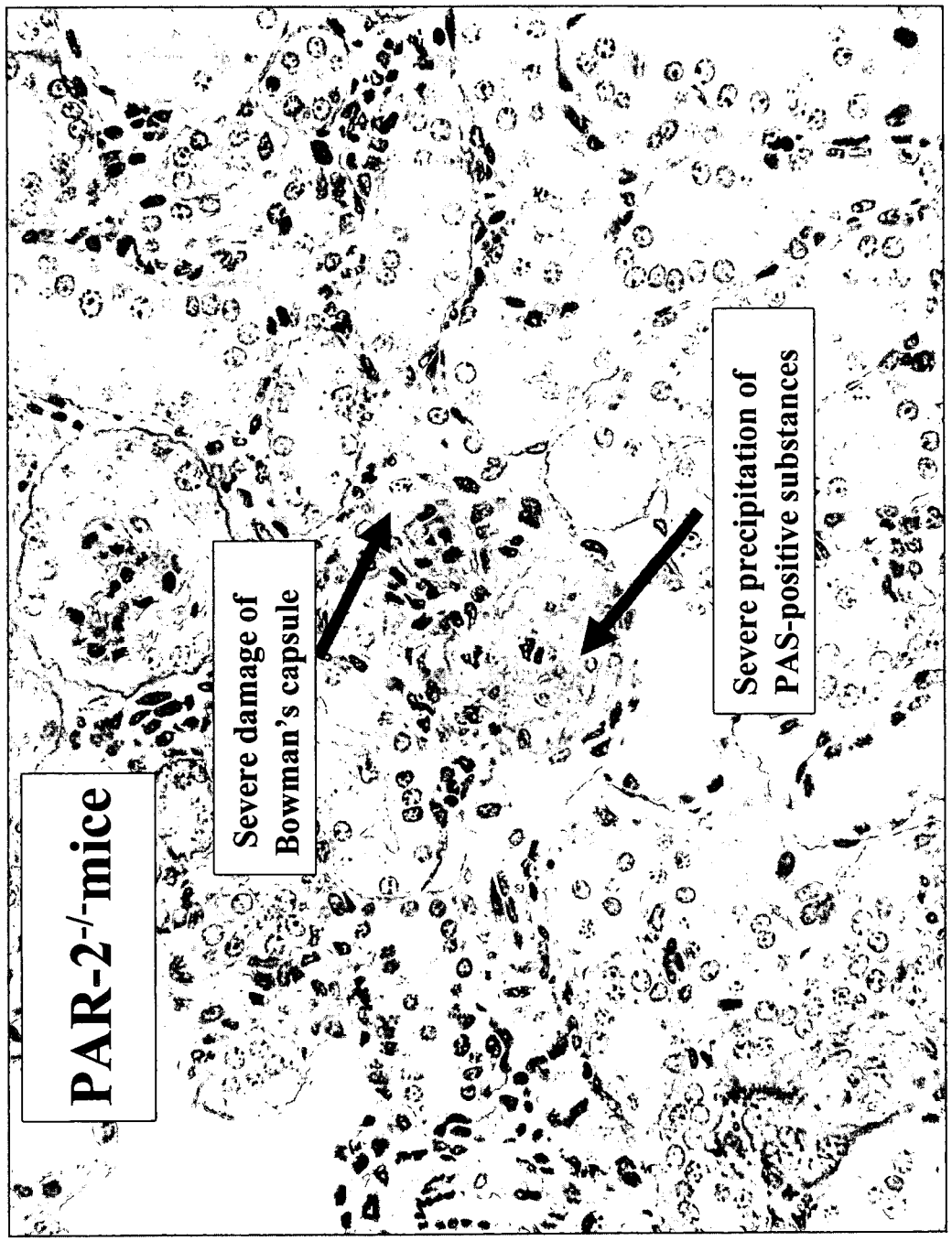

Further, pathological tissues of kidney excised from the mouse after completion of the experiment was investigated. The histopathological images where the diseased site was stained with Periodic acid Schiff (PAS) are shown in FIG. 2 as photographic pictures. FIG. 2(a) is a picture for the wild type mouse while FIG. 2(b) is a picture for the PAR-$2^{-/-}$ mouse. As compared with the wild type mouse, there were observed severe precipitation of PAS-positive substances and severe damage of Bowman's capsule in the PAR-$2^{-/-}$ mouse. Incidentally, precipitation of the PAS-positive substances and damage of Bowman's capsule are positioned as pathological indexes of nephritis.

Figure 3A:
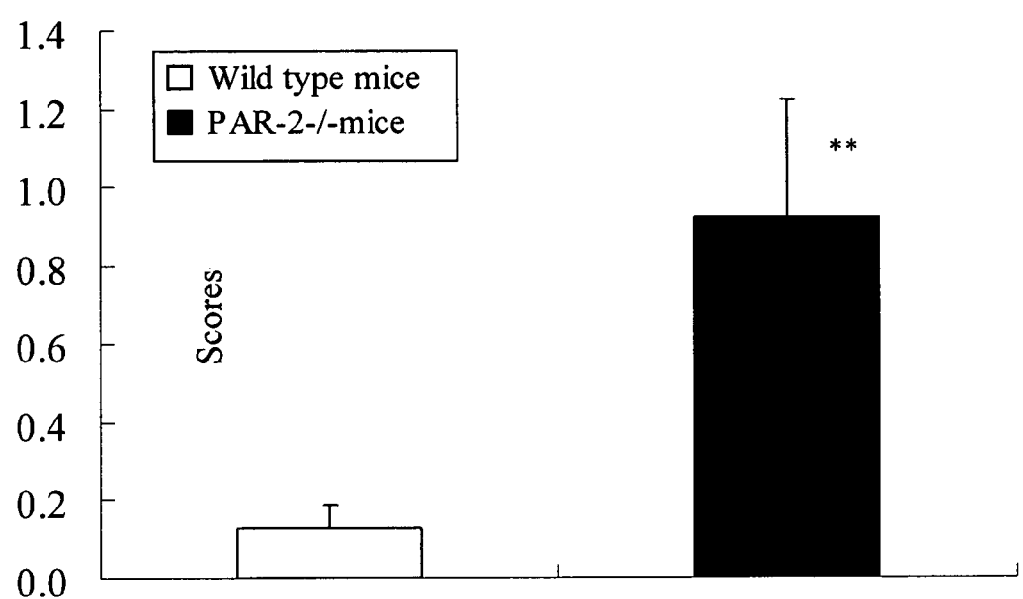
FIG. 3(a) shows data where degree of precipitation of PAS-positive substance in kidney is scored in wild type mouse and PAR-$2^{-/-}$ mouse after five weeks from induction of nephritis.
Figure 3B:
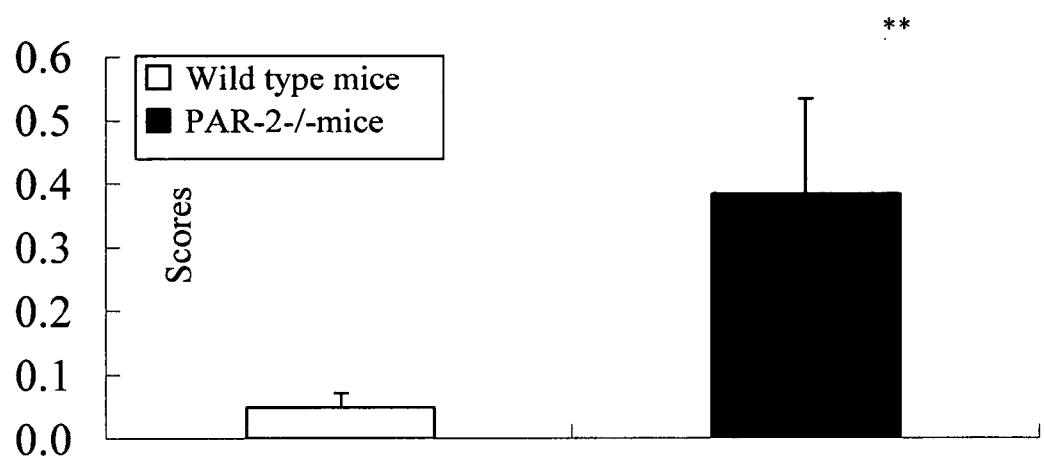
FIG. 3(b) shows data where degree of damage of Bowman's capsule is scored in wild type mouse and PAR-$2^{-/-}$ mouse after five weeks from induction of nephritis.

Result of the degree of precipitation of the PAS-positive substances in terms of numerals is shown in FIG. 3(a). The ordinate of FIG. 3(a) shows the score while white square and black square of FIG. 3(a) in the abscissa show the cases of the wild type mouse and the PAR-$2^{-/-}$ mouse, respectively. Each of the values in FIG. 3(a) shows mean value ± standard error of the score and  shows that there is a statistically significant difference of $p<0.01$ in comparison with the wild type mouse. As a result, severer precipitation of PAS-positive substances was noted in the PAR-$2^{-/-}$ mouse. Result of the degree of damage of Bowman's capsule in terms of numerals is shown in FIG. 3(b). The ordinate of FIG. 3(b) shows the score while white square and black square of FIG. 3(b) of the abscissa show the cases of the wild type mouse and the PAR-2$^{-/-}$ mouse, respectively. Each of the values in FIG. 3(b) shows mean value ± standard error of the score and  shows that there is a statistically significant difference of p<0.01 in comparison with the wild type mouse. As a result, severer damage of Bowman's capsule was noted in the PAR-2$^{-/-}$ mouse.

From those results, there was suggested a possibility that deficiency of PAR-2 gene worsens the nephritis both functionally and pathologically, in other words, that activation of PAR-2 is effective for prevention and treatment of nephritis.

On the basis of those results, the present inventors have further investigated the therapeutic effect of activation of PAR-2 on nephritis.

Anti-GBM antiserum was administered to the wild type mice to induce nephritis, the mice were classified into three groups and the first group was administered with a peptide having an amino acid sequence of SLIGRL which is a selective stimulant for PAR-2 while the second group was administered with prednisolone which has been used as a treating agent for nephritis. In each group, administration was conducted once daily for consecutive seven days. The third group was a group which was not treated with a drug (control group). Further, for comparison, another untreated group where no anti-GBM antiserum was administered was prepared as the fourth group (in each group, n=6).

Figure 4:
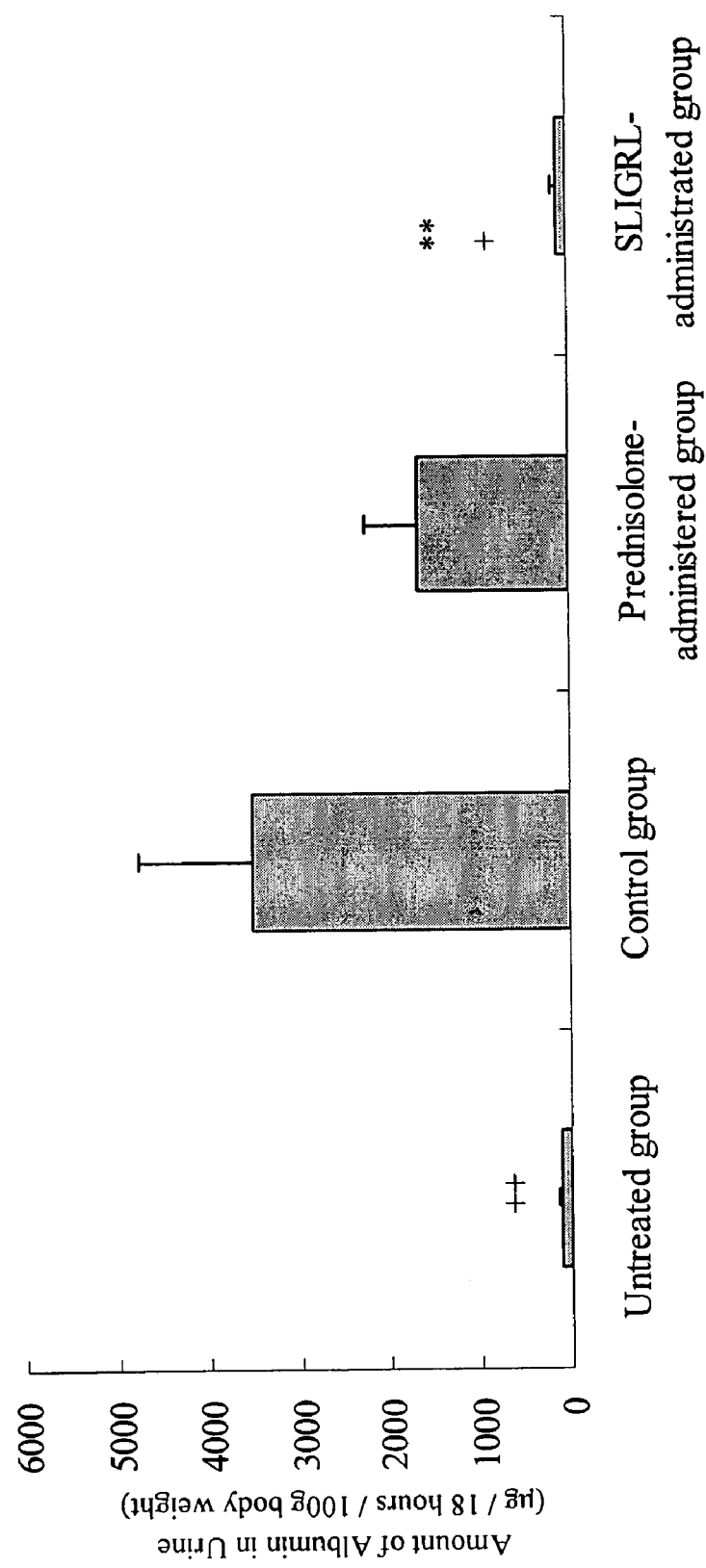
FIG. 4 shows the effect of a PAR-2 activating agent (SLIGRL which is a selective agonist) and that of prednisolone which is a steroids in wild type mouse where nephritis was induced.

Immediately after the final administration of the drug solution, urine was collected for 18 hours and the amount of albumin in urine was measured. The result is shown in FIG. 4. The ordinate of FIG. 4 shows the amount of albumin in urine (μg/18 hours/100 g body weight) and the abscissa shows untreated group (the fourth group), control group (the third group), prednisolone-administered group (the second group) and SLIGRL-administered group (the first group) from left to right. Each value in FIG. 4 shows mean value ± standard error, ** shows that there is a statistically significant difference of p<0.01 in comparison with the control group, + means that there is a statistically significant difference of p<0.05 in comparison with the prednisolone-administered group (the second group) and ++ means that there is a statistically significant difference of p<0.01 in comparison with the prednisolone-administered group (the second group).

As a result, as compared with the amount of albumin in urine of the untreated group (the fourth group) where no anti-GBM antiserum was administered, that of the control group (the third group) showed significantly high data. By administration of SLIGRL which is a selective stimulant for PAR-2, the amount of albumin in urine decreased significantly and drastically (97.0%). In addition, administration of 3 mg/kg of prednisolone which has been known to have a suppressive effect to an increase in albumin amount in urine reduced the amount of albumin in urine to an extent of 52.7% of the control group but it was not a significant suppression.

In the same manner, anti-GBM antiserum was administered to the wild type mice to induce nephritis, the mice were classified into three groups and the first group was administered with ASKH95 which is a selective stimulant for PAR-2 while the second group was administered with prednisolone which has been used as a treating agent for nephritis. In each group, administration was conducted once daily for consecutive seven days. The third group was a group which was not treated with a drug (control group) (in each group, n=6).

Figure 5:
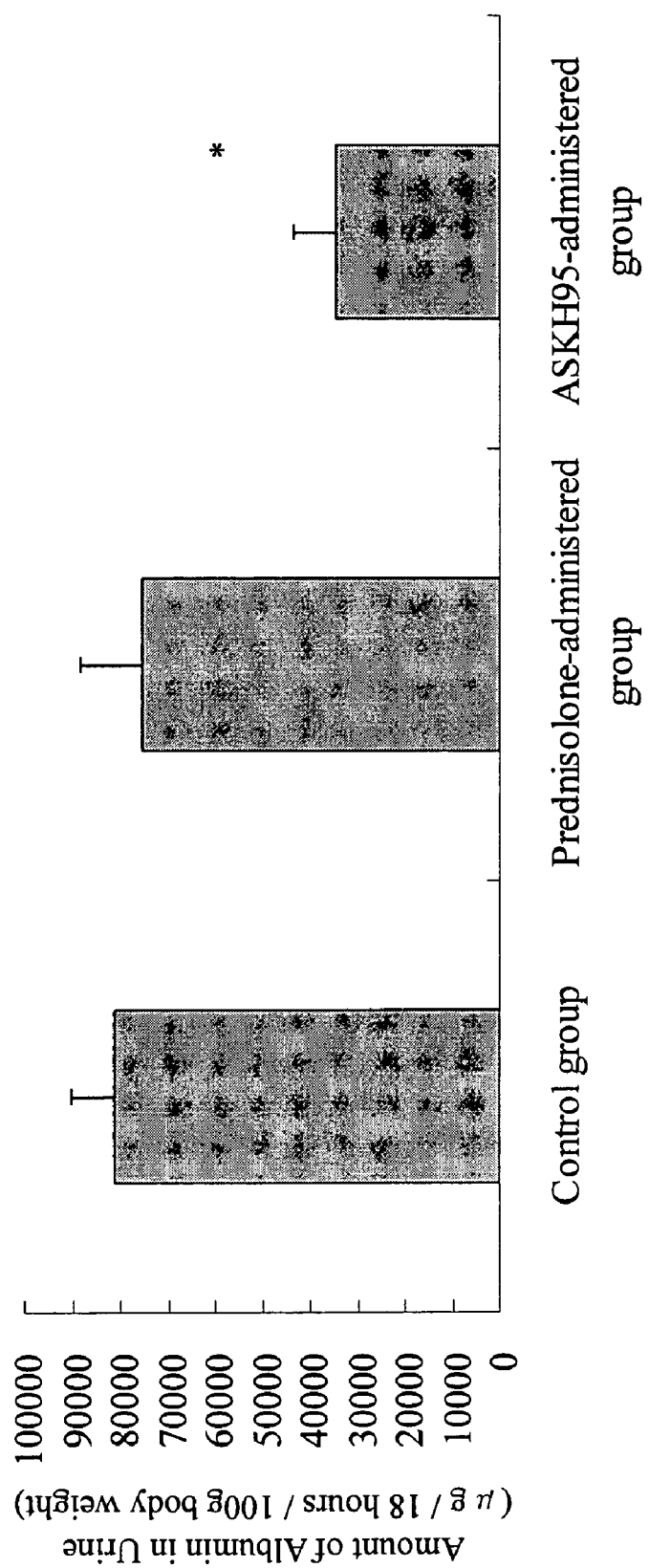
FIG. 5 shows the effect of a PAR-2 activating agent (ASKH95 which is a selective agonist) and that of prednisolone which is a steroids in wild type mouse where nephritis was induced.

Immediately after the final administration of the drug solution, urine was collected for 18 hours and the amount of albumin in urine was measured. The result is shown in FIG. 5. The ordinate of FIG. 5 shows the amount of albumin in urine (μg/18 hours/100 g body weight) and the abscissa shows control group (the third group), prednisolone-administered group (the second group) and ASKH95-administered group (the first group) from left to right. Each value in FIG. 5 shows mean value ± standard error, * shows that there is a statistically significant difference of p<0.05 in comparison with the control group.

As a result, as compared with the amount of albumin in urine of the control group (the third group), the amount of albumin in urine decreased significantly by administration of ASKH95 which is a selective stimulant for PAR-2. On the other hand, administration of 3 mg/kg of prednisolone had almost no effect on the amount of albumin in urine as compared with the control group.

Accordingly, SLIGRL which is a peptide and ASKH95 are stimulants for PAR-2 being a kind of PAR-2 activators were confirmed to be highly effective for prevention and treatment of renal diseases such as nephritis as a result of the experiments and was found that prevention and treatment of renal diseases such as nephritis can be conducted very effectively by activation of PAR-2. Moreover, the resulting beneficial effects were found to be stronger than prednisolone which is a steroids being commonly used at present in clinic for the treatment of nephritis.

With regard to the activator for PAR-2 according to the present invention, anything may be acceptable so far as it is able to active the function of PAR-2 and there may be used a PAR-2 stimulator which is able to activate its function by stimulating PAR-2, a PAR-2 gene expression enhancer which is able to activate the function of PAR-2 by enhancing expression of PAR-2 gene, etc. as the PAR-2 activator for the present invention. Specific examples of the PAR-2 activator of the present invention are PAR-2 ligand, PAR-2 ligand derivative (for example, ASKH95, etc.), trypsin, tryptase, tissue factor/VIIa factor, Xa factor, acrosin and trypsin-like serine protease, etc. To be more specific, examples of the peptide or its derivative having an amino acid sequence which activates the receptor of cleaved site of PAR-2 are peptides having at least an amino acid sequence of LIG (according to a one-letter expression of amino acids), preferably peptides comprising 3 to 8 amino acids having an amino acid sequence of LIG (according to a one-letter expression of amino acids) and, more preferably, peptides having an amino acid sequence of SLIGKV (according to a one-letter expression of amino acids) and SLIGRL (according to a one-letter expression of amino acids) or ASKH95. Incidentally, ASKH95 is a PAR-2 ligand derivative described in the literature (J. Clin. Invest. 111, 35-41, 2003), the compound is shown as 2-furoyl-LIGKV-OH.

As mentioned above, the PAR-2 activators of the present invention show an excellent suppressive action to nephritis in mouse nephritis models and such PAR-2 activators are useful as agents for prevention and treatment of renal diseases.

The preventive agent and the composition for treatment of kidney diseases according to the present invention contain the above PAR-2 activator as an effective ingredient and is able to be manufactured by manufacturing methods which have been known and common among persons skilled in the art as a composition suitable for dosage form such as oral or parenteral agent, e.g., oral agents, injection agents, suppositories, ointments and plasters by compounding with pharmaceutically acceptable carriers.

In preparing a solid preparation for oral administration, an example is that excipients and, if necessary, binders, disintegrating agents, lubricants, coloring agents, corrigents for taste and smell, etc. are added to the above PAR-2 activator followed by subjecting to a common method whereupon tablets, coated tablets, granules, powders, capsules, etc. are able to be manufactured. With regard to such additives, those which have been commonly used in the related field may be used and, for example, lactose, white sugar, sodium chloride, glucose, starch, calcium carbonate, kaolin, microcrystalline cellulose, silicic acid, etc. may be exemplified as excipients;

water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone, etc. may be exemplified as binders; dry starch, sodium alginate, agar powder, sodium hydrogen carbonate, calcium carbonate, sodium laurylsulfate, stearic acid monoglyceride, lactose, etc. may be exemplified as disintegrating agents; pure talc, stearate, borax, polyethylene glycol, etc. may be exemplified as lubricants; and white sugar, dried orange peel, citric acid, tartaric acid, etc. may be exemplified as corrigents for taste.

In preparing a liquid preparation for oral use, an example is that corrigents for taste, buffers, stabilizers, corrigents for smell, etc. are added to the above PAR-2 followed by subjecting to a common method whereupon liquid preparation for oral use, syrup, elixir, etc. are able to be manufactured. In this case, the already-mentioned ones may be exemplified as corrigents for taste; sodium citrate, etc. may be exemplified as buffers; and tragacanth, gum arabic, gelatin, etc. may be exemplified as stabilizers.

In preparing an injection preparation, an example is that pH adjusting agents, buffers, stabilizers, isotonizing agents, local anesthetics, etc. are added to the above PAR-2 followed by subjecting to a common method whereupon hypodermic, intramuscular and intravenous injection preparations are able to be manufactured. In this case, sodium citrate, sodium acetate, sodium phosphate, etc. may be exemplified as pH adjusting agents and buffers; sodium pyrosulfite, EDTA, thioglycolate, thiolactic acid, etc. may be exemplified as stabilizers; procaine hydrochloride, lidocaine hydrochloride, etc. may be exemplified as local anesthetics; and sodium chloride, glucose, etc. may be exemplified as isotonizing agents.

Other preparations may also be prepared in accordance with known methods.

The preventive and treating agents for kidney diseases according to the present invention thus prepared are effective for prevention and treatment of all kidney diseases where lesion is noted in kidney. They are particularly effective for prevention and treatment of clinically classified primary (protopathic) nephritis such as acute nephritis syndrome, rapidly progressive glomerulo nephritis syndrome, relapsing and continuous hematuria and chronic nephritis syndrome and secondary nephritis such as nephrotic syndrome; and histopathologically classified primary (protopathic) nephritis such as primary glomerular disease including diffuse glomerulo nephritis group [mild glomerular lesion group, focal/local lesion group and membranous glomerulo nephritis, membrano proliferative glomerulo nephritis, mesangial proliferative glomerulo nephritis (IgA nephropathy, etc.), intraductal proliferative glomerulo nephritis, mesangial capillary glomerulo nephritis, high-density precipitation glomerulo nephritis, crescentic (extratubal) glomerulo nephritis, sclerosing glomerulo nephritis, etc.] and secondary nephritis such as glomerular disease based on systematic disease (lupus nephritis, Goodpasture syndrome, etc.), glomerular diseases based on vascular disease (glomerular thrombosis, etc.), glomerular disease based on metabolic diseases (diabetic nephropathy, amyloidosis, etc.), hereditary renal lesion (Alport's syndrome, etc.), transplanted glomerular lesion, etc.

Although the dose of the agent for prevention and treatment of renal diseases according to the present invention may vary depending upon body weight, age, sex and symptom of the patient, dosage form, frequency of administration, etc., it is usually preferred to administer 0.01 to 1000 mg or, more preferably, 0.1 to 100 mg per day of the above PAR-2 activator to an adult once daily or by diving into several times a day either orally or parenterally.

The present invention also provides a method for screening an effective ingredient for prevention and treatment of kidney diseases where a PAR-2 activating action of a test substance is screened.

There is no particular limitation for the screening method of the present invention and there may be exemplified the methods mentioned in various literatures such as a cell assay where changes in intracellular $Ca^{2+}$ concentration using incubated cells, etc. which express PAR-2 such as human umbilical vein endothelial cell or COS-1 into which PAR-2 gene is introduced (*J. Biol. Chem.*, 272, 11133-11141, 1997) or production of phosphorylated inositol (*Proc. Natl. Acad. Sci. USA*, 94, 8884-8889, 1997) are/is used as an index and a function analysis such as detection of endothelium-dependent vasorelaxant reaction in artery of rat (*Can. J. Physiol. Pharmacol.*, 73, 1203-7, 1995) or detection of secretion of mutin from salivary gland of rat (*Biochemical and Biophysical Research Communications*, 270, 298-302, 2000).

EXAMPLES

The present invention will now be illustrated in detail by way of the following Examples although the present invention is not limited thereto.

Example 1

Effect of deficiency of PAR-2 gene on nephritis induced by antiglomerular basement membrane (anti-GBM) antibody was investigated. In the experiment, there were used self-bred male PAR-2 gene deficient mouse (PAR-$2^{-/-}$ mouse) which is a hybrid of self-proliferated 13-weeks-age C57BL/6 with 129/O1a and a wild type one thereof.

Nephritis was induced by a single administration of anti-rabbit antiserum (anti-GBM antiserum) to mouse GBM having about 16-fold of titer of antibody in an amount of 0.4 ml per mouse into tail vein (*Jpn. J. Pharmacol.*, 33, 1145-1154, 1983). With regard to the amount of albumin in urine used as an index for nephritis, the amount of albumin in urine collected for 18 hours using a metabolic cage (manufactured by Sugiyamagen) was determined using an ELISA kit manufactured by Exocel and expressed in terms of μg/18 hours/100 g body weight. The resulting data were analyzed by a Student t-test and evaluated.

Results of measurement of the albumin amount in urine after 1, 2, 3 and 5 weeks from administration of anti-GBM antiserum in the wild type mice and the PAR-$2^{-/-}$ mice are shown in FIG. 1 (8 mice were used for each group). Incidentally, the albumin amounts in urine of untreated wild type mice and PAR-$2^{-/-}$ mice to which no anti-GBM antiserum was administered were 99.2±27.9 (n=6) and 222.9±63.9 (n=6), respectively and there was no statistically significant difference between them.

The amount of albumin in urine of PAR-$2^{-/-}$ mice to which anti-GBM antiserum was administered significantly increased after one week from administration of the anti-GBM antiserum as compared with that of the wild type mice (wild type mice: 1441.2±840.4; PAR-$2^{-/-}$ mice: 4689.2±787.1) and, after two and three weeks and even after five weeks (wild type mice: 3094.9±1834.7; PAR-$2^{-1}$ mice: 46462.2±7255.5), significant increase was still noted.

As a result, it was noted that deficiency of PAR-2 gene worsened nephritis significantly in terms of functions and also that it progressed the degree of nephritis with the passage of time.

Example 2

Histopathological images of kidney excised from the mouse after completion of the experiment of Example 1 and data where precipitation of PAS (periodic acid Schiff)-positive substance which was a pathological index for nephritis and damage of Bowman's capsule were made into scores are shown in FIG. 2(a) (b) and FIG. 3(a)(b), respectively. Incidentally, GBM, mesangial matrix, basement membranes of Bowman's capsule and tubule, proximal convoluted tubule epithelium brush border, etc. were well identified as a result of staining using PAS and precipitation of glycoprotein including immune complex was able to be observed as well. The method was carried out as follows. Thus, according to the known report (*Kidney Blood Press Res.*, 24, 27-32, 2001), excised kidney was fixed with a neutrally buffered formalin solution and embedded in paraffin, the resulting slice having a thickness of 2 mm was stained with PAS and pathological damage was evaluated under an optical microscope and scored. In the kidney of the wild type mice after five weeks from administration of anti-GBM antiserum, there were resulted pathological failures such as precipitation of PAS-positive substances and damage of Bowman's capsule (arrows in FIG. 2(a)) and, in the PAR-2$^{-/-}$ mice, such pathological damages were more significant (arrows in FIG. 2(b)). In addition, in the comparison of the data where such pathological observations were scored, the PAR-2$^{-/-}$ mice showed significantly higher values than the wild type mice concerning precipitation of the PAS-positive substances (FIG. 3(a); wild type mice: 0.13±0.06, PAR-2$^{-/-}$ mice: 0.92±0.30) and damage of Bowman's capsule (FIG. 3(b); wild type mice: 0.05±0.02, PAR-2$^{-/-}$ mice: 0.8±0.15).

From the results of Example 1 and Example 2, it was noted that deficiency of PAR-2 gene deteriorated nephritis both functionally (Example 1) and pathologically (Example 2).

From the results of Example 1 and Example 2, possibility that PAR-2 activator is effective for nephritis was suggested and, therefore, therapeutic effect of the PAR-2 stimulant for nephritis was then investigated.

Example 3

Anti-GBM antiserum was administered to a wild type mouse and, immediately after that, 0.3 μmol/kg of SLIGRL which is a selective stimulant for PAR-2 dissolved in a phosphate buffer or 3 mg/kg of prednisolone suspended in 0.5% methyl cellulose solution was administered thereto once daily for consecutive seven days (in each group, n=6). SLIGRL was administered to tail vein with a dose of 1 ml/100 g body weight at the rate of 0.1 ml/second. Prednisolone was compulsorily administered per os with a dose of 1 ml/100 g body weight. As a control, a group which was not treated with a drug (control group) was set up. As from immediately after the final administration of the drug solution, urine was collected for 18 hours using a metabolic cage and the amount of albumin in urine was measured. The result is shown in FIG. 4.

Like Example 1, as compared with the amount of albumin (99.2±27.9) in urine of the untreated group where no anti-GBM antiserum was administered, that of the control group was significantly high (3528.5±1238.6). By administration of SLIGRL which is a selective stimulant for PAR-2, the amount of albumin in urine significantly and drastically (97.0%) decreased (104.2±54.0). Administration of 3 mg/kg of prednisolone which has been recognized to have a suppressive action to an increase of albumin in urine reduced the amount of albumin in urine to an extent of 52.7%(1670.6±579.4) of that of the control group but it was not a significant suppression.

Example 4

In the same manner as example 3, anti-GBM antiserum was administered to a wild type mouse and, immediately after that, 10 mg/kg of ASKH95 which is a selective stimulant for PAR-2 dissolved in a phosphate buffer or 3 mg/kg of prednisolone suspended in 0.5% methyl cellulose solution was administered thereto once daily for consecutive seven days (in each group, n=6). ASKH95 was administered to tail vein with a dose of 1 ml/100 g body weight at the rate of 0.1 ml/second. Prednisolone was compulsorily administered per os with a dose of 1 ml/100 g body weight. As a control, a group which was not treated with a drug (control group) was set up. As from immediately after the final administration of the drug solution, urine was collected for 18 hours using a metabolic cage and the amount of albumin in urine was measured. The result is shown in FIG. 5. Incidentally, ASKH95 is synthesized according to the literature (*J. Clin. Invest.* 111, 35-41, 2003), and used.

Like Example 3, as compared with the amount of albumin (81319.0±8884.3) in urine of the control group, the amount of albumin (34709.6±8703.3) in urine decreased significantly by administration of ASKH95 which is a selective stimulant for PAR-2. On the other hand, administration of 3 mg/kg of prednisolone had almost no effect on the amount of albumin (75692.1±12846.9) in urine as compared with the control group.

It has been accordingly found that a stimulant for PAR-2 is effective for suppression of nephritis and that its effect is stronger than prednisolone which is a steroids commonly used for the treatment of nephritis in clinic at present.

INDUSTRIAL APPLICABILITY

The present invention is able to provide a method for prevention and treatment of kidney diseases where an activator for PAR-2 represented by a stimulant for PAR-2, an enhancer for expression of PAR-2 gene or the like is an effective ingredient, and also able to provide a method for screening an effective ingredient for prevention and therapy of kidney diseases where an activating action of a test substance for PAR-2 is screened.

The invention claimed is:

1. A method for treatment of rapidly progressive glomerulonephritis syndrome or crescentic (extratubular) glomerulonephritis which comprises administering a composition for treatment of rapidly progressive glomerulonephritis syndrome or crescentic (extratubular) glomerulonephritis containing a PAR-2 (Protease-activated receptor-2) activating agent as an effective ingredient to a patient suffering from rapidly progressive glomerulonephritis syndrome or crescentic (extratubular) glomerulonephritis.

2. The method according to claim 1, wherein the activator for PAR-2 is a PAR-2 ligand, a PAR-2 ligand derivative, trypsin, tryptase, tissue factor/VIIa factor, Xa factor, acrosin or a trypsin-like serine protease.

\* \* \* \* \*